United States Patent
Pouchoulin

(10) Patent No.: US 11,020,517 B2
(45) Date of Patent: Jun. 1, 2021

(54) TREATMENT SOLUTION DELIVERY IN AN EXTRACORPOREAL BLOOD TREATMENT APPARATUS

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 331 days.

(21) Appl. No.: 15/913,231

(22) Filed: Mar. 6, 2018

(65) Prior Publication Data

US 2018/0193544 A1    Jul. 12, 2018

Related U.S. Application Data

(63) Continuation of application No. 14/386,062, filed as application No. PCT/IB2013/052202 on Mar. 20, 2013, now Pat. No. 9,931,452.

(60) Provisional application No. 61/613,575, filed on Mar. 21, 2012.

(30) Foreign Application Priority Data

Mar. 21, 2012    (EP) .................................. 12001975

(51) Int. Cl.
    *A61M 1/16*    (2006.01)

(52) U.S. Cl.
    CPC ............ *A61M 1/1605* (2014.02); *A61M 1/16* (2013.01); *A61M 1/1601* (2014.02); *A61M 1/1613* (2014.02); *A61M 1/1643* (2014.02); *A61M 2205/3334* (2013.01); *A61M 2205/3379* (2013.01); *A61M 2205/3393* (2013.01); *A61M 2205/3396* (2013.01); *A61M 2205/50* (2013.01)

(58) Field of Classification Search
    None
    See application file for complete search history.

(56) References Cited

U.S. PATENT DOCUMENTS

| | | |
|---|---|---|
| 3,888,126 A | 6/1975 | Cross |
| 4,267,041 A | 5/1981 | Schael |
| 4,372,846 A | 2/1983 | Yamagami |
| 4,713,171 A | 12/1987 | Polaschegg |
| 4,769,132 A | 9/1988 | Patono |
| 4,859,319 A | 8/1989 | Borsari |
| 4,894,150 A | 1/1990 | Schurek |
| 4,994,026 A | 2/1991 | Fecondini |
| 5,043,074 A | 8/1991 | Chevallet |
| 5,441,636 A | 8/1995 | Chevallet |
| 5,650,071 A | 7/1997 | Brugger |
| 5,672,481 A | 9/1997 | Minshall |

(Continued)

FOREIGN PATENT DOCUMENTS

| | | |
|---|---|---|
| DE | 3801316 A1 | 7/1988 |
| DE | 9403081 U1 | 6/1994 |

(Continued)

*Primary Examiner* — Michael H. Wilson
*Assistant Examiner* — Katherine A Will
(74) *Attorney, Agent, or Firm* — Mueting Raasch Group

(57) ABSTRACT

Blood treatment apparatus and methods of using the same are described herein that include two or more intermediate containers located between a treatment solution source and a port through which the treatment solution is to be delivered with the blood treatment apparatus. The weight of the intermediate containers is measured and used to control the refilling and emptying of treatment solution in the intermediate containers.

26 Claims, 8 Drawing Sheets

(56) References Cited

U.S. PATENT DOCUMENTS

| | | |
|---|---|---|
| 5,725,775 A | 3/1998 | Bene |
| 5,993,657 A | 11/1999 | Williams |
| 6,039,877 A | 3/2000 | Chevallet |
| 6,042,784 A | 3/2000 | Wamsiedler |
| 6,561,996 B1 | 5/2003 | Gorsuch |
| 6,561,997 B1 | 5/2003 | Weitzel |
| 6,818,179 B1 | 11/2004 | Edgson |
| 7,153,286 B2 | 12/2006 | Busby |
| 2004/0133145 A1 | 7/2004 | Bene |
| 2004/0167457 A1 | 8/2004 | Tonelli |
| 2004/0238416 A1 | 12/2004 | Burbank |
| 2004/0267183 A1 | 12/2004 | Chevallet |
| 2007/0007208 A1 | 1/2007 | Brugger |

FOREIGN PATENT DOCUMENTS

| | | |
|---|---|---|
| EP | 1543853 A1 | 9/1985 |
| EP | 0722744 A1 | 7/1986 |
| EP | 0213050 A1 | 3/1987 |
| EP | 0796997 A1 | 9/1997 |
| EP | 2019296 A1 | 1/2009 |
| FR | 2472936 A1 | 7/1981 |
| FR | 2594340 A1 | 2/1986 |
| FR | 765258 A | 12/1993 |
| JP | 53083397 A | 7/1978 |
| JP | 5937959 A | 3/1984 |
| WO | WO 99/19007 | 4/1999 |

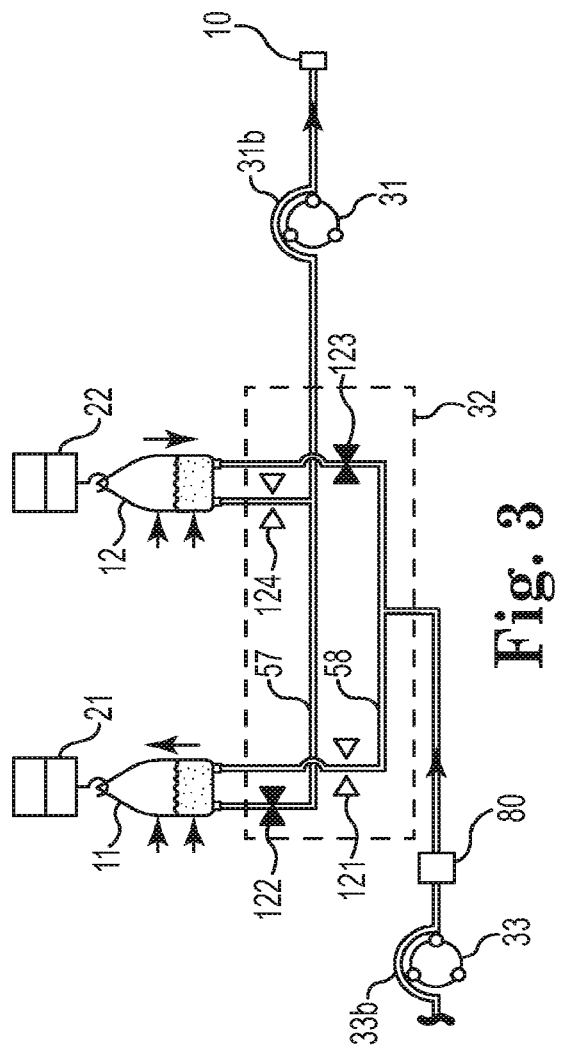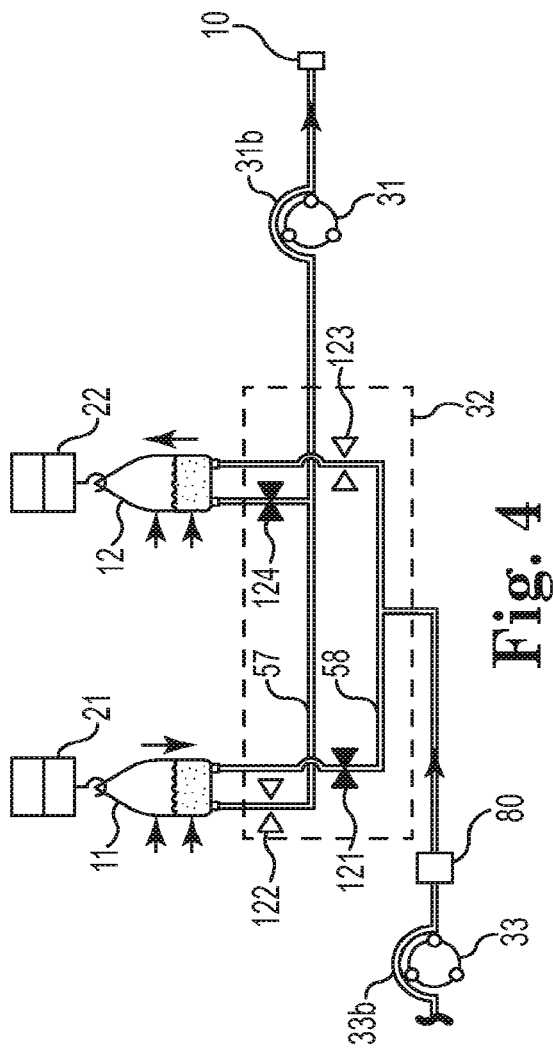

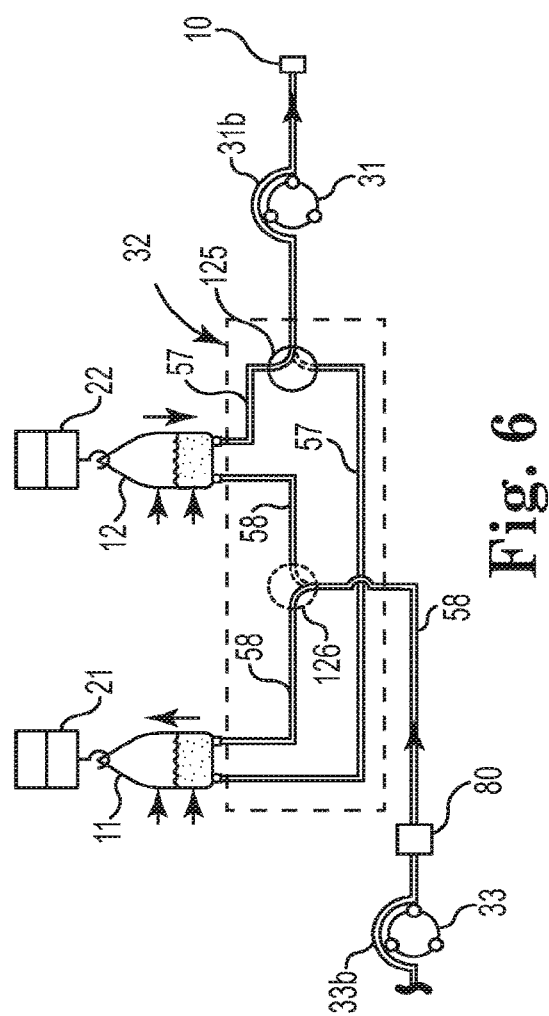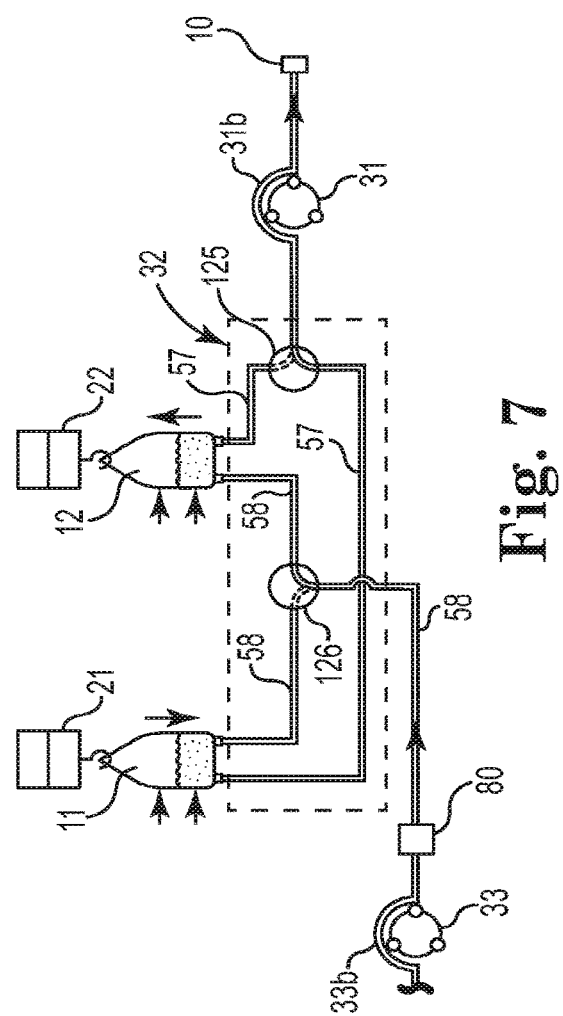

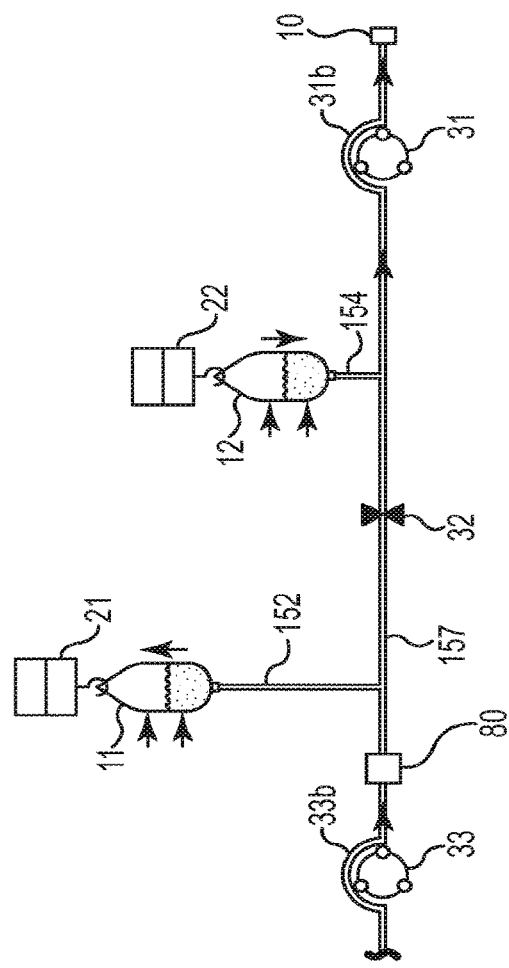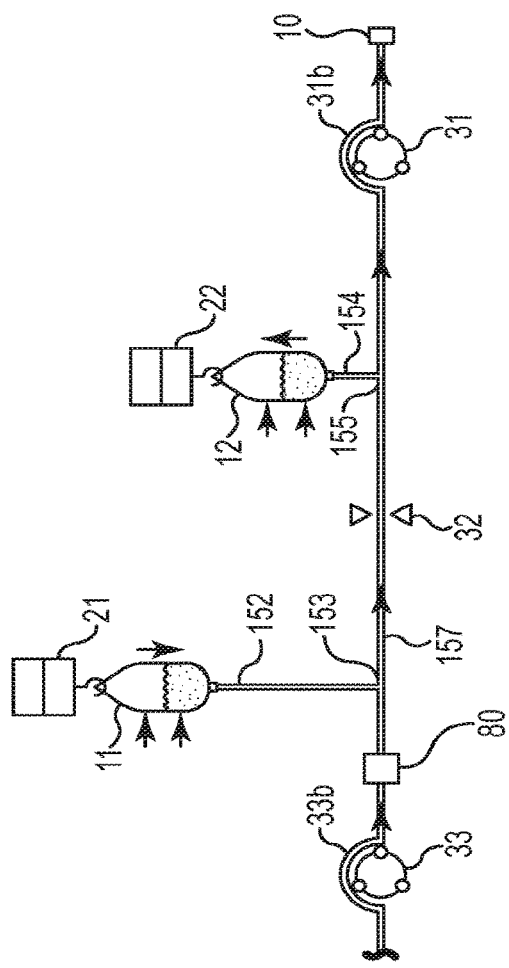

TREATMENT SOLUTION DELIVERY IN AN EXTRACORPOREAL BLOOD TREATMENT APPARATUS

This application is a continuation of U.S. application Ser. No. 14/386,062, filed Sep. 18, 2014, which is a U.S. National Stage Application of International Application No. PCT/IB2013/052202, filed Mar. 20, 2013, which was published in English on Sep. 26, 2013 as International Patent Publication WO 2013/140346 A1, which claims the benefit under 35 U.S.C. 119(e) of U.S. Provisional Application No. 61/613,575 filed Mar. 21, 2012. International Application No. PCT/IB2013/052202 also claims priority to European Application No. 12001975.7 filed Mar. 21, 2012. A certified copy of European Application No. 12001975.7 filed Mar. 21, 2012, was provided in, and is available in, U.S. patent application Ser. No. 14/386,062, filed Sep. 18, 2014, for which certified copy is available in PAIR Apparatus and methods for delivering treatment solution in an extracorporeal blood treatment apparatus and associated methods are described herein.

BACKGROUND

Extracorporeal blood treatment means taking the blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment is used with patients incapable of effectively eliminating matter from their blood, for example in the case of a patient who is suffering from temporary or permanent kidney failure. These and other patients may undergo extracorporeal blood treatment to add to or to eliminate matter from their blood, to maintain an acid-base balance or to eliminate excess body fluids, for instance.

Extracorporeal blood treatment is typically performed by sampling the patient's blood in a continuous flow, by introducing the blood into a primary chamber of a filter that is defined, at least in part, by a semi-permeable membrane. The semi-permeable membrane may selectively allow the unwanted matter contained in the blood pass through the membrane, from the primary chamber to the secondary chamber, and may selectively allow the beneficial matter contained in the liquid going into the secondary chamber pass through the membrane to the blood going into the primary chamber, according to the type of treatment.

A number of extracorporeal blood treatments may be performed by the same machine. In ultrafiltration (UF) treatment, the unwanted matter is eliminated from the blood by convection through the membrane in the secondary chamber.

In hemofiltration (HF) treatment, the blood runs through a chamber that is defined, at least in part, by a semi-permeable membrane as in UF, and the beneficial matter is added to the blood, typically by the introduction of a fluid into the blood, either before, or after its passage through the filter and before it is returned to the patient.

In hemodialysis (HD) treatment, a secondary fluid containing the beneficial matter is introduced into the filter's secondary chamber. The blood's unwanted matter crosses the semi-permeable membrane by diffusion and penetrates into the secondary fluid, and the beneficial matter of the secondary fluid can cross the membrane and penetrate into the blood.

In hemodiafiltration (HDF) treatment, the blood and the secondary fluid exchange their matter as in HD, and further, matter is added to the blood, typically by introducing a fluid into the treated blood before it is returned to the patient as in HF; unwanted matters are eliminated from the blood by convection and diffusion.

In those treatments using a secondary fluid, the secondary fluid goes through the filter's secondary chamber and receives the blood's unwanted matter by diffusion and/or convection through the membrane. This liquid is then extracted from the filter: it is commonly called effluent, and is sent to a drain or to a receptacle then intended to be discharged into a drain.

In the extracorporeal treatments that use a secondary fluid, the secondary fluid may be supplied in a sterile single-use bag as illustrated in FIG. 1. For purposes of this discussion, the secondary fluid may be dialysate contained in a dialysate bag 11. The dialysate bag 11 delivers dialysate to the secondary chamber 4 through an exit line 9. This bag 11 is combined with a gravimetric scale 21 linked to a control unit 41. Thus, weight signals are transmitted to the control unit 41 that is capable of monitoring the weight changes of the bag 11 and to control a pump 31 acting on the exit line 9 (i.e., the line delivering dialysate from the bag 11 to the secondary chamber 4).

In some embodiments, however, a session can last several days and the single-use dialysate bag 11 is emptied well before the end of the session. This phenomenon is all the more pronounced during an intensive treatment. Indeed, one wishes both to exchange a large quantity of liquid in HF or HDF therapy, and to perform long-term treatments.

As soon as the bag 11 reaches a set level (or at another time as selected by a user), the pump acting on the exit line 9 (and other pumps as needed) may be temporarily stopped, while the blood continues to circulate extracorporeally in the filters primary chamber 3. Once the pump 31 is stopped, the user has to disconnect and unhook the empty dialysate bag 11. Then the user attaches and connects a new full single-use bag 11 to the treatment apparatus and restarts the pump(s) to return to the extracorporeal treatment with fluid circulation through the two chambers (3, 4) of the filter 2.

This bag replacement operation has several potential disadvantages. The operation is performed by health care personnel who have to monitor several patients at the same time (a waiting time before action by the personnel typically increases therapy down time and may require additional treatment time or result in decreased treatment efficiency), the regular changing of the dialysate bag during a session adds an economic cost to the treatment, and the bags are heavy and relatively fragile objects to handle and can potentially be perforated while handling.

Although described herein in connection with the delivery of dialysate, it should be understood that similar issues may be encountered in blood treatment apparatus in which infusion fluids are delivered into the blood (whether before or after filter or before the blood pump). For purposes of the discussions herein, any such fluids will be referred to as "treatment solutions" which may include, e.g., dialysate; a replacement fluid of a convective replacement therapy of the renal function; plasma, albumin or colloid solutions that may be used in Therapeutic Plasma Exchange (TPE); or any other known type of medical fluid for replacement therapy.

SUMMARY

The blood treatment apparatus described herein include two or more intermediate containers that are located between a treatment solution source and a port through which the treatment solution is to be delivered with the blood treatment apparatus. The weight of the intermediate containers is measured and used to control the refilling and emptying of treatment solution in the intermediate containers. The use of two or more intermediate containers as described herein at a location between the treatment solution source and the remainder of the blood treatment apparatus may reduce or eliminate the need to halt delivery of the treatment solution to change the intermediate containers as they are emptied and/or refilled. As a result, significant increases in uninterrupted treatment duration may be possible.

The amount of treatment solution delivered to the selected portion of the blood treatment apparatus is typically controlled based on the weight of the treatment solution delivered to the output controller as determined by the gravimetric scales described herein. In some embodiments, the flow rate of the treatment solution through the output controller may also be controlled, at least in part, based on the weight changes of the intermediate containers.

In one aspect, some embodiments of the blood treatment apparatus described herein include: a blood circuit that includes an arterial line intended to draw blood from a patient and a venous line intended to return blood to the patient; and a treatment solution delivery system configured to deliver treatment solution within the blood treatment apparatus through a treatment solution port. The treatment solution delivery system may include: a first gravimetric scale configured to weigh a first intermediate container; a second gravimetric scale configured to weigh a second intermediate container; a source flow controller configured to deliver treatment solution from a treatment solution source to a first intermediate container weighed by the first gravimetric scale and to a second intermediate container weighed by the second gravimetric scale; an output controller configured to control the flow of treatment solution from the first intermediate container and the second intermediate container to the treatment solution port; a container selection controller located in a treatment solution path between the source flow controller and the output controller; a control unit operably attached to the first gravimetric scale, the second gravimetric scale, the source flow controller, the container selection controller, and the output controller. The control unit is configured to: receive weight signals from the first and second gravimetric scales; control the source flow controller, the container selection controller, and the output controller in a first mode in which treatment solution is delivered to the output controller while treatment solution leaves the first intermediate container and the second intermediate container fills with treatment solution; control the source flow controller, the container selection controller, and the output controller in a second mode in which the second intermediate container delivers treatment solution to the output controller while the first intermediate container fills with treatment solution from the treatment solution source.

In some embodiments of the blood treatment apparatus described herein, the control unit is configured to control the source flow controller, the container selection controller, and the output controller such that a continuous flow of treatment solution is provided to the treatment solution port when switching between the first mode and the second mode.

In some embodiments of the blood treatment apparatus described herein, the blood treatment apparatus comprises a filter having a primary chamber and a secondary chamber separated by a semi-permeable membrane, wherein the blood circuit is configured to pass blood through the primary chamber, and wherein the treatment solution port is configured to deliver treatment solution to the secondary chamber.

In some embodiments of the blood treatment apparatus described herein, the treatment solution port is configured to deliver treatment solution to blood in the blood circuit.

In some embodiments of the blood treatment apparatus described herein, the apparatus includes an air detector located between the treatment solution source and the first and second intermediate containers such that treatment solution delivered to the first intermediate container and the second intermediate container from the treatment solution source passes through the air detector.

In some embodiments of the blood treatment apparatus described herein, the apparatus comprises a sterilizing filter located between the treatment solution source and the treatment solution port such that treatment solution delivered to the treatment solution port from the treatment solution source passes through the sterilizing filter. In some embodiments, a sterilizing filter is located between the treatment solution source and the first and second intermediate containers such that treatment solution delivered to the first intermediate container and the second intermediate container from the treatment solution source passes through the sterilizing filter.

In some embodiments of the blood treatment apparatus described herein, the apparatus includes a source flow controller located between the treatment solution source and the first and second intermediate containers such that treatment solution delivered to the first intermediate container and the second intermediate container from the treatment solution source passes through the source flow controller. A sterilizing filter may be located between the source flow controller and the first and second intermediate containers such that treatment solution delivered to the first intermediate container and the second intermediate container from the treatment solution source passes through the sterilizing filter. The sterilizing filter (if included) may have a passive air vent that comprises a hydrophobic membrane.

In some embodiments of the blood treatment apparatus described herein, the treatment solution source comprises a plurality of supply reservoirs.

In some embodiments of the blood treatment apparatus described herein, the treatment solution source comprises a liquid source, treatment solution precursor, and mixing apparatus configured to combine liquid from the liquid source and the treatment solution precursor to form the treatment solution.

In some embodiments of the blood treatment apparatus described herein, the container selection controller comprises a valve configured to have an open state in which flow through a line on which the valve acts is allowed and a closed state in which flow through a line on which the valve acts is prevented.

In some embodiments of the blood treatment apparatus described herein, the container selection controller comprises a pump configured to deliver treatment solution through a line on which the pump is located when the pump is operating and to prevent flow of treatment solution through the line on which the pump is located when the pump is not operating.

In some embodiments of the blood treatment apparatus described herein, the container selection controller comprises a multi-port valve, wherein in a first configuration the multi-port valve allows treatment solution from the treatment solution source to flow into the first intermediate container and prevent the treatment solution from flowing into the second intermediate container, and wherein in a second configuration the multi-port valve allows treatment solution from the treatment solution source to flow into the second intermediate container and prevent the treatment solution from flowing into the first intermediate container.

In some embodiments of the blood treatment apparatus described herein, the first intermediate container outlet flow controller and the second intermediate container outlet flow controller comprise a multi-port valve, wherein in a first configuration the multi-port valve allows treatment solution from the first intermediate container to flow to the output controller and prevent flow of treatment solution from the second intermediate container to the output controller, and wherein in a second configuration the multi-port valve allows treatment solution from the second intermediate container to flow to the output controller and prevent flow of treatment solution from the first intermediate container to the output controller.

In some embodiments of the blood treatment apparatus described herein, the control unit is configured to calculate, from the received weight signals, the amount of treatment solution delivered to the output controller from both the first intermediate container and the second intermediate container.

In another aspect, some embodiments of the methods of controlling treatment solution flow in a blood treatment apparatus may include: filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level; and delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level.

The blood treatment apparatus used to practice some embodiments of the methods described herein may be any of the various embodiments of blood treatment apparatus described herein.

In some embodiments, the methods described may include filling the second intermediate container with treatment solution by delivering treatment solution from the treatment solution source to the second intermediate container, weighing the second intermediate container to determine when the amount of treatment solution in the second intermediate container has risen to a selected fill level, and halting the delivery of treatment solution to the second intermediate container when the amount of treatment solution in the second intermediate container has risen to the selected fill level; and delivering treatment solution from the first intermediate container to the output controller while filling the second intermediate container from the treatment solution source, weighing the first intermediate container to determine when the amount of treatment solution in the first intermediate container has fallen to a selected refill level, and halting the delivery of treatment solution to the output controller when the amount of treatment solution in the first intermediate container has fallen to the selected refill level.

In some embodiments, the methods described herein may include replacing one or more supply reservoirs of a plurality of supply reservoirs in the treatment solution source while delivering treatment solution to the first intermediate container or the second intermediate container.

In some embodiments, the methods described herein may include constituting treatment solution from a treatment solution precursor and a liquid source in the treatment solution source while delivering treatment solution to the first intermediate container or the second intermediate container.

In some embodiments of the methods described herein the treatment solution is delivered substantially continuously to the output controller.

In some embodiments, the methods described herein may include passing the treatment solution from the treatment solution source through an air detector when delivering treatment solution from the treatment solution source to the first intermediate container or the second intermediate container.

In some embodiments, the methods described herein may include passing the treatment solution from the treatment solution source through a sterilizing filter when delivering treatment solution from the treatment solution source to the first intermediate container or the second intermediate container.

In some embodiments of the methods described herein, filling the first intermediate container or the second intermediate container comprises pumping treatment solution from the treatment solution source through a source flow controller to the first intermediate container or the second intermediate container.

In some embodiments of the methods described herein, the amount of treatment solution delivered to the output controller from both the first intermediate container and the second intermediate container is calculated based on weight of the first and second intermediate containers.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the blood treatment apparatus described herein. Rather, a more complete understanding of the invention will become apparent and appreciated by reference to the following Description of Illustrative Embodiments and claims in view of the accompanying figures of the drawing.

BRIEF DESCRIPTION OF THE VIEWS OF THE DRAWING

FIG. 3 depicts a first operating mode of the extracorporeal blood treatment apparatus of FIG. 2 in which the first intermediate container is filled from the treatment solution source while the second intermediate container delivers treatment solution to the output controller.

FIG. 4 depicts a second operating mode of the extracorporeal blood treatment apparatus of FIG. 2 in which the second intermediate container is filled from the treatment solution source while the first intermediate container delivers treatment solution to the output controller.

FIG. 6 depicts a first operating mode of the extracorporeal blood treatment apparatus of FIG. 5 in which the first intermediate container is filled from the treatment solution source while the second intermediate container delivers treatment solution to the output controller.

FIG. 7 depicts a second operating mode of the extracorporeal blood treatment apparatus of FIG. 5 in which the second intermediate container is filled from the treatment solution source while the first intermediate container delivers treatment solution to the output controller.

FIG. 9 depicts a first operating mode of the extracorporeal blood treatment apparatus of FIG. 8 in which the first intermediate container is filled from the treatment solution source while the second intermediate container delivers treatment solution to the output controller.

FIG. 10 depicts a second operating mode of the extracorporeal blood treatment apparatus of FIG. 8 in which the second intermediate container is filled while the first intermediate container delivers treatment solution to the output controller.

DESCRIPTION OF ILLUSTRATIVE EMBODIMENTS

Figure 1:
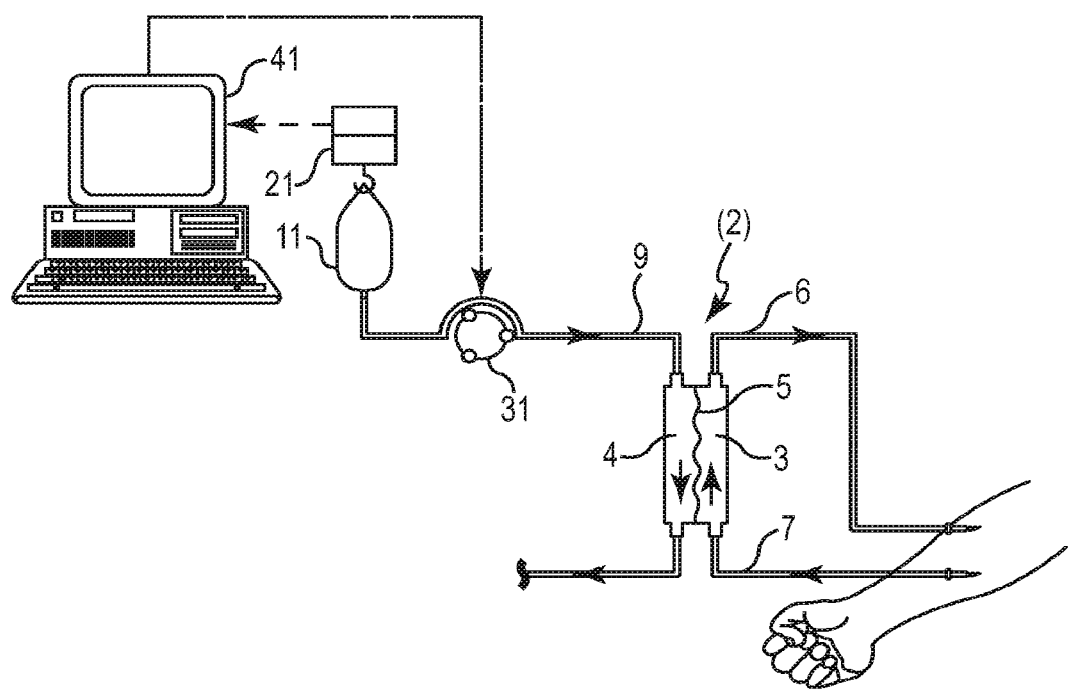
FIG. 1 depicts a known extracorporeal blood treatment apparatus.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Figure 2:
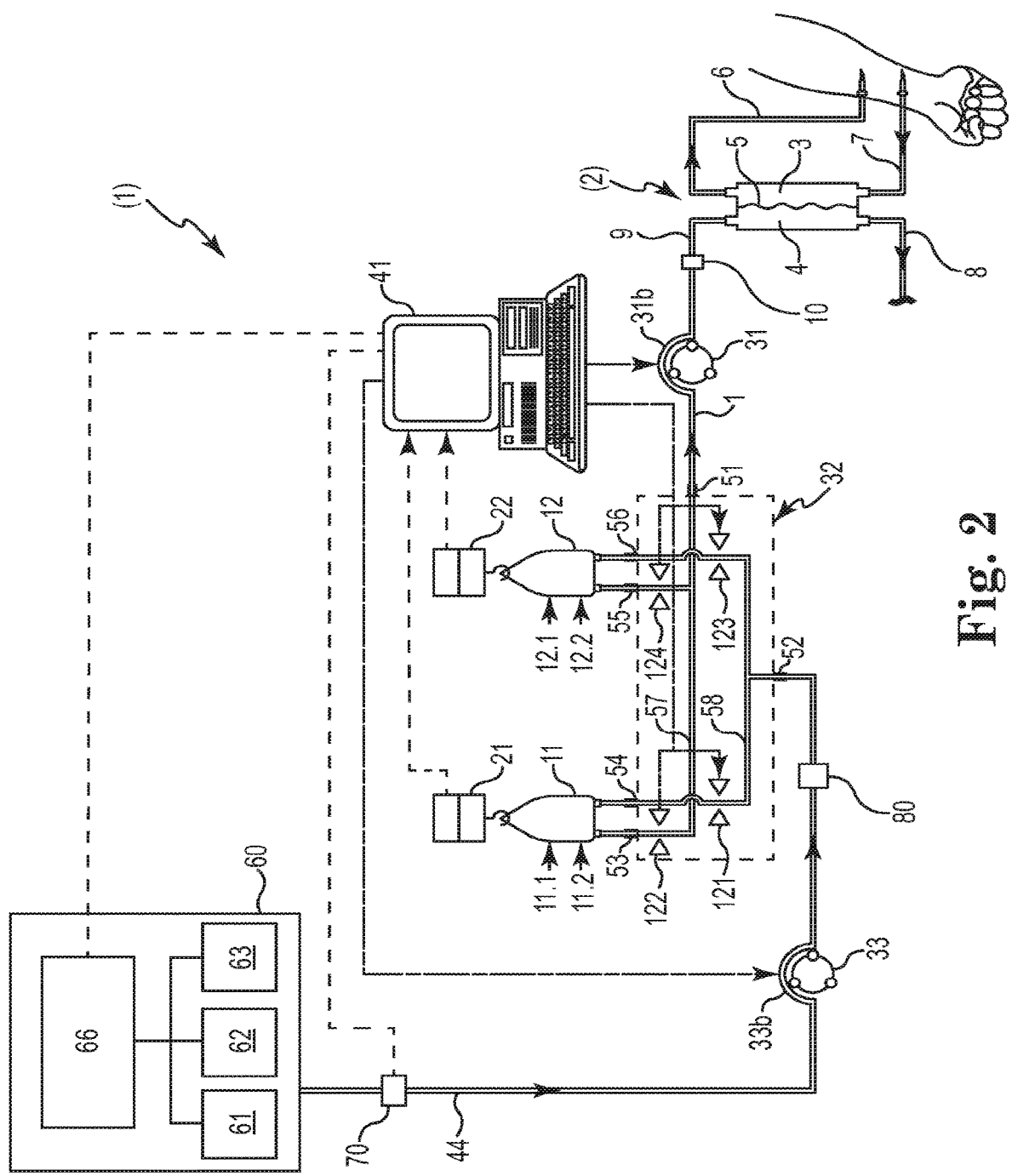
FIG. 2 depicts one embodiment of an extracorporeal blood treatment apparatus as described herein.
Figure 5:
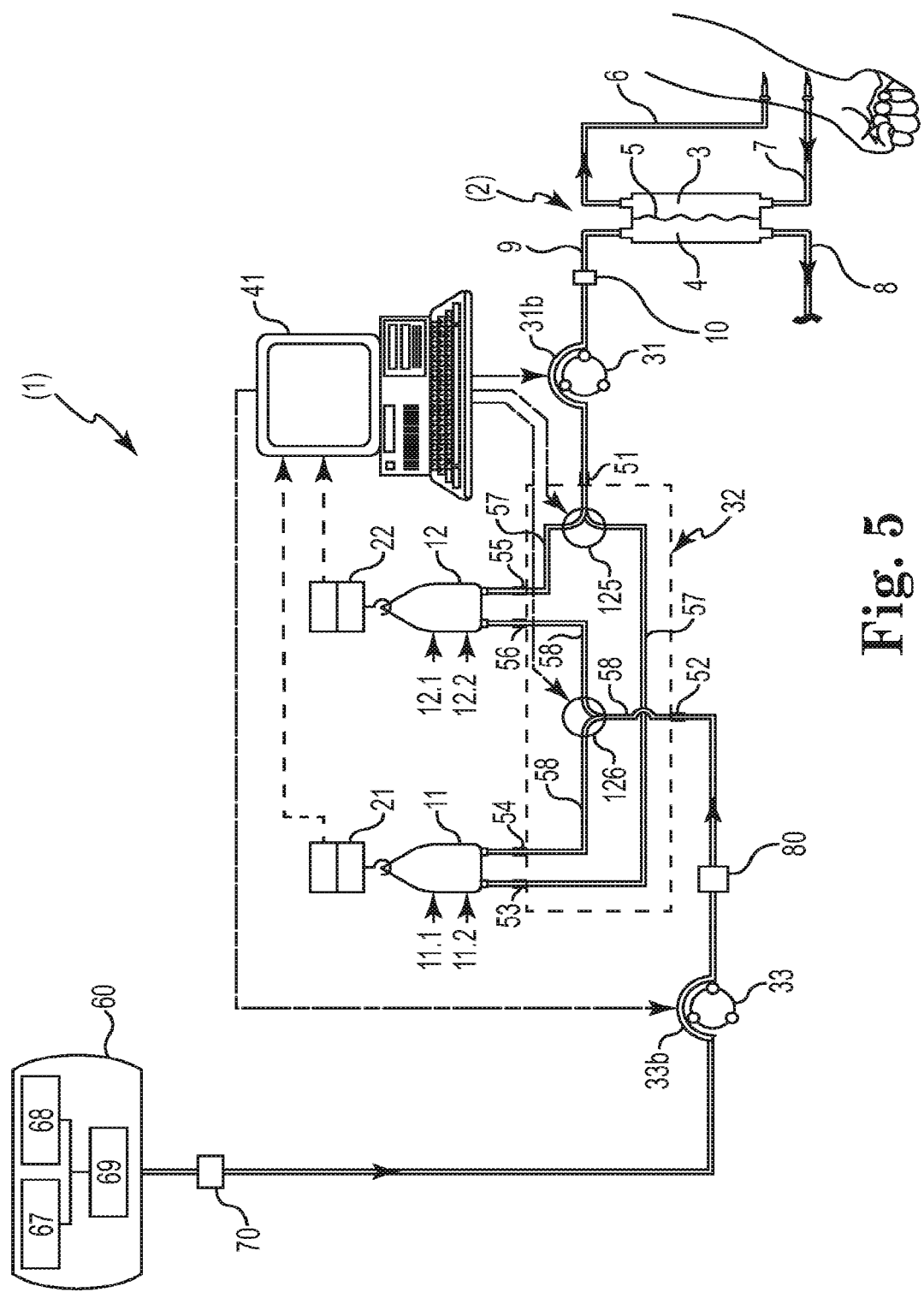
FIG. 5 depicts another embodiment of an extracorporeal blood treatment apparatus as described herein.
Figure 8:
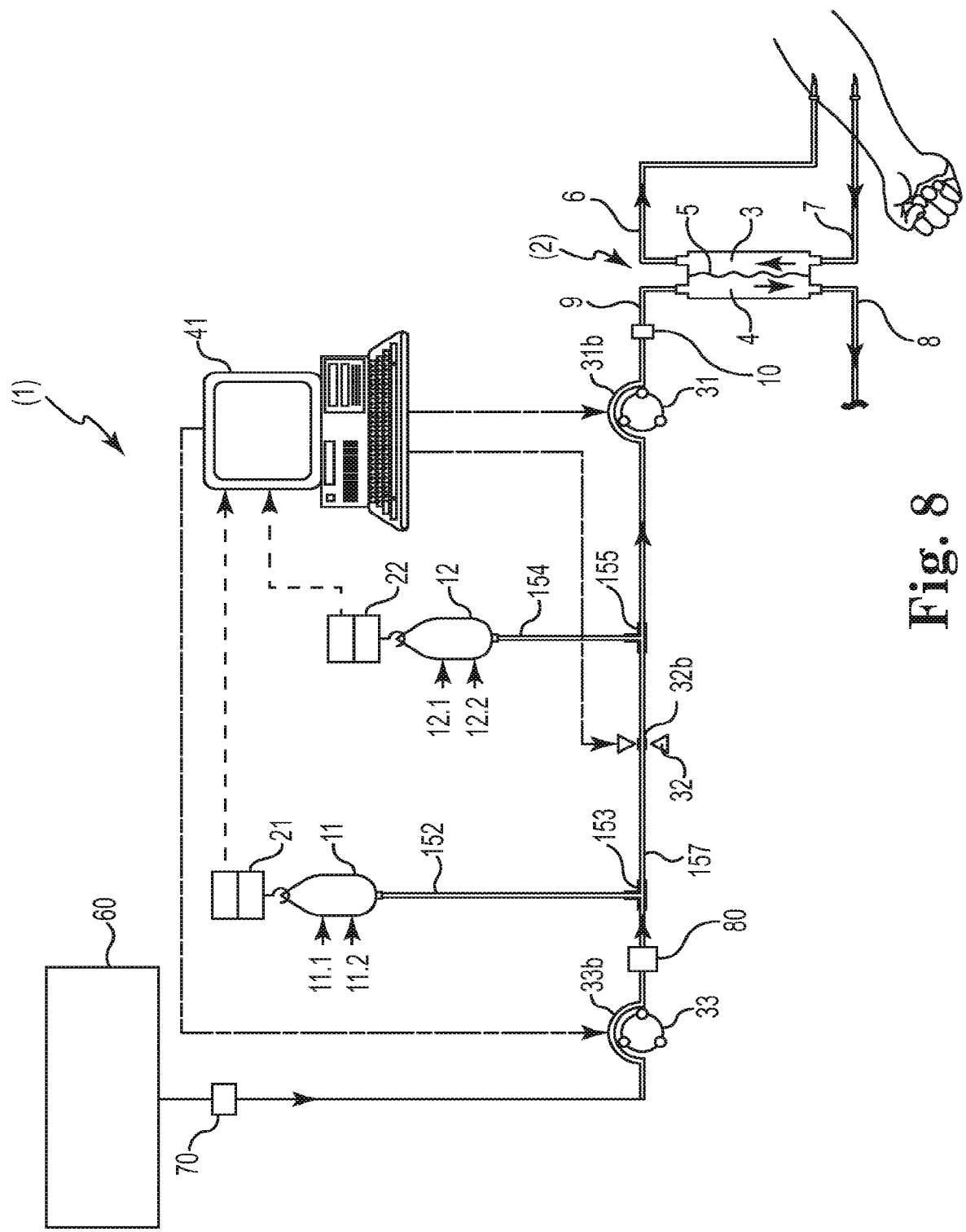
FIG. 8 depicts another embodiment of an extracorporeal blood treatment apparatus as described herein.

In the various illustrative embodiments of FIGS. 2, 5, and 8, a blood treatment apparatus 1 is depicted. The depicted blood treatment device 1 is in an operational configuration that enables it to perform a hemodialysis treatment. The other treatment configurations mentioned previously (ultrafiltration, hemofiltration and hemodiafiltration) are of course possible within other embodiments, and the principles, systems, and methods described herein may be applied in those embodiments as well.

The blood treatment apparatus 1 depicted in FIGS. 2, 5, and 8 includes a filter 2 having a primary chamber 3 and a secondary chamber 4 separated by a semi-permeable membrane 5. A blood circuit in the blood treatment apparatus 1 includes an arterial line 7 intended to draw blood from the patient, the filter's primary chamber 3 and a venous line 6 intended to return blood to the patient from the primary chamber 3.

Treatment solution (e.g., dialysate, etc.) is delivered to the blood treatment apparatus 1 in each embodiment. Because the treatment solution in each of the depicted embodiments is dialysate, the treatment solution is delivered to the secondary chamber 4 of the filter 2 through a treatment solution port 10 connected to inlet line 9 using output controller 31. Liquids are removed from the secondary chamber 4 of the filter 2 through a drain line 8.

Although the output controller 31 is, in the embodiments of FIGS. 2, 5, and 8 depicted in the form of a peristaltic pump, the output controller 31 may be provided in a variety of alternative forms that can be used to control the flow of the treatment solution including, e.g., other pumps (e.g., piston pumps, diaphragm pumps, etc.), other flow control mechanisms (e.g., valves, clamps, etc.), etc.

Although each embodiment of the blood treatment apparatus depicted in FIGS. 2, 5, and 8 involves delivery of treatment solution (in the form of, e.g., dialysate) to the secondary chamber 4 of the filter 2 through treatment solution port 10 connected to inlet line 9, other treatment solutions may, in other embodiments, be delivered directly to blood in the arterial line 7 and/or venous line 6 (or even, in some embodiments, into the blood resident in primary chamber 3).

In still other embodiments, the blood treatment apparatus as described herein may include the delivery of two or more different treatment solutions to the same or different locations within the blood treatment apparatus. For example, treatment solution in the form of dialysate may be delivered to the secondary chamber 4 of the filter as depicted in the embodiments of FIGS. 2, 5, and 8 while one or more different treatment solutions are delivered to, e.g., the blood in primary chamber 3, arterial line 7, and/or venous line 6.

The treatment solution delivered by the treatment solution delivery system within the blood treatment apparatus described herein is supplied using two or more intermediate containers. The weight of the intermediate containers can be measured and may be used to control the refilling and emptying of treatment solution in the intermediate containers. In some embodiments, the amount of treatment solution delivered to the selected portion of the blood treatment apparatus can also be controlled, at least in part, based on the weight and/or weight changes of the intermediate containers. The treatment solution in the two or more intermediate containers is provided to the intermediate containers from a treatment solution source which may potentially reduce or eliminate the need to halt delivery of the treatment solution to change the intermediate containers as they are emptied and/or refilled.

In the blood treatment apparatus described herein, the "intermediate containers" may take any suitable form in which liquids can be stored, e.g., bags, bottles, reservoirs, etc.

In the embodiments of the blood treatment apparatus 1 depicted in FIGS. 2, 5, and 8, a first intermediate container 11 and a second intermediate container 12 are used to supply treatment solution to the output controller 31 that, in turn, supplies treatment solution to the treatment solution port 10 that, in the depicted embodiment, is connected to inlet line 9. A first gravimetric scale 21 is configured to weigh the first intermediate container 11, with the weight being indicative of the amount of treatment solution contained in the first intermediate container 11. A second gravimetric scale 22 is configured to weigh the second intermediate container 12, with the weight being indicative of the amount of treatment solution contained in the second intermediate container 12.

Another feature common to the illustrative embodiments of the blood treatment apparatus depicted in FIGS. 2, 5, and 8 is a control unit 41 is linked to the first gravimetric scale 21 and the second gravimetric scale 22, as well as the output controller 31. Regardless of the additional fluid flow control components that may or may not be present in the blood treatment apparatus described herein, the control unit 41 may be linked to the various fluid flow control components (in addition to the first gravimetric scale 21, the second gravimetric scale 22, and the output controller 31) such that one of the intermediate containers (11, 12) is filled with treatment solution while treatment solution exits from the other intermediate container (12, 11), and vice-versa.

The control unit 41 may be provided in any suitable form and may, for example, include memory and a controller. The controller may, for example, be in the form of one or more microprocessors, Application Specific Integrated Circuit (ASIC) state machines, etc. The control units 41 may include a variety of any suitable input devices configured to allow a user to operate the apparatus (e.g., keyboards, touchscreens, mice, trackballs, etc.), as well as display devices configured to convey information to a user (e.g., monitors (which may or may not be touchscreens), indicator lights, etc.).

More particularly, the blood treatment apparatus described herein include an output controller 31 acting downstream from the first intermediate container 11 and the second intermediate container 12. The control unit 41 may be configured to control the output controller 31 to provide substantially continuous flow of the treatment solution to the treatment solution port 10 during the treatment delivered using the blood treatment apparatus. The various fluid flow control components and reservoirs found in the apparatus are controlled to provide substantially continuous flow of treatment solution through the treatment solution port 10 (at a constant flow rate and/or at a variable flow rate according to a selected flow rate profile).

The weight information supplied to the control unit 41 by the first gravimetric scale 21 is used to monitor the weight of the first intermediate container 11 so as both to know the amount of treatment solution flowing out of the first intermediate container 11, and to control the loading and unloading phase of the first and second intermediate containers 11, 12 by using two preselected threshold values (e.g., 11.1 and 11.2) that can be set based on the volume of each intermediate container.

The second gravimetric scale 22 provides weight information to the control unit 41 so that the weight of the second intermediate container 12 can be monitored. That weight information can be used to determine the amount of treatment solution flowing out of the second intermediate container 12. That weight information can also be used to control the cyclic loading and unloading process by using one or two threshold values (e.g., 12.1 and 12.2) for the second gravimetric scale together with one or two threshold values (11.1 and 11.2) for the first gravimetric scale. If the use of two threshold values is enough for control of treatment solution flow control, the four threshold values of the two gravimetric scales can, in some embodiments, be used for other functions such as, e.g., preventive alarm purposes concerning an abnormal state for a bag, etc.

In some embodiments, the control unit 41 is configured to calculate the amount of treatment solution delivered to blood treatment apparatus from the treatment solution source 60 based on the weight signals received from gravimetric scales that are configured to weigh each of the intermediate containers used to deliver fluid to the output controller 31 (which, in the depicted embodiments includes first and second gravimetric scales (21 and 22), but could include more gravimetric scales if more than two intermediate containers are used to feed the output controller 31).

Each of the illustrative embodiments of the blood treatment apparatus depicted in FIGS. 2, 5, and 8 includes a treatment solution source 60 that provides treatment solution to the intermediate containers that are, in turn, used to supply treatment solution to the output controller 31. The treatment solution source 60 is in fluid communication with a container selection controller 32 that can be used to direct treatment solution from the treatment solution source 60 to the first intermediate container 11 or the second intermediate container depending on which intermediate container needs to be refilled. The treatment solution source 60 supplies treatment solution to the container selection controller 32 through a source flow controller 33.

Although the source flow controller 33 is, in the embodiments of FIGS. 2, 5, and 8 depicted in the form of a peristaltic pump, the source flow controller 33 may be provided in a variety of alternative forms that can be used to control the flow of the treatment solution including, e.g., other pumps (e.g., piston pumps, diaphragm pumps, etc.), other flow control mechanisms (e.g., valves, clamps, etc.), etc.

The treatment solution in the treatment solution source 60 may, in the embodiment depicted in FIG. 2, include a plurality of reservoirs 61, 62, 63 that can be independently replaced to ensure that the treatment solution source 60 can continue to provide treatment solution to the container selection controller 32. The reservoirs 61, 62, 63 can take any form suitable for containing a delivering a liquid such as, e.g., bags, bottles, etc. The reservoirs 61, 62, 63 may be adapted for a single use (after which they would be disposed of), but the reservoirs 61, 62, 63 could be refillable when they are not connected within the treatment solution source 60 to deliver treatment solution.

In some embodiments, all of the reservoirs 61, 62, 63 may be in fluid communication with the source flow controller 33 at the same time, while in other embodiments, it may be possible to selectively place one or more of the reservoirs 61, 62, 63 in fluid communication with the source flow controller 33 while one or more of the reservoirs 61, 62, 63 are not in fluid communication with the source flow controller 33 (they may be, e.g., disconnected, or have a fluid line that is closed by a valve, clamp, or other flow controller).

Although the treatment solution source 60 depicted in FIG. 2 includes three reservoirs 61, 62, 63, other embodiments may be operated with as few as one or two reservoirs, while still other embodiments of the treatment solution source may be provided with four or more reservoirs containing treatment solution. Also, in some embodiments, the reservoirs may all contain the same volume of liquid or they may contain different volumes of the treatment solution.

In some embodiments, the treatment solution source 60 includes a reservoir fill monitor 66 that is configured to monitor the fill status of the reservoirs 61, 62, 63 (either individually or collectively). The fill monitor 66 may monitor the fluid volumes using any suitable technique or combination of techniques, e.g., using weight, using capacitive, optical, or other sensors, using fluid pressure (in, e.g., line 44), etc. The fill monitor 66 may potentially be operably linked to the control unit 41 such that when a reservoir 61, 62, 63 needs to be refilled, the blood treatment apparatus 1 can provide an alert or indicator (e.g., visible, audible, etc.) so that appropriate action can be taken. If the fill status of the reservoirs 61, 62, 63 is monitored collectively, then any alert or indicator may be activated when the collective amount of treatment solution in the reservoirs 61, 62, 63 reaches a selected lower limit, e.g., a limit of ⅓ of the maximum amount of treatment solution that would be contained in three reservoirs (implying that at least one of the reservoirs 61, 62, 63 may need to be replaced, refilled, etc.).

Another optional feature found in the embodiments of the blood treatment apparatus 1 depicted in FIGS. 2, 5, and 8 is an air detector 70 that may be located in the fluid delivery line 44 leading from the treatment solution source 60 to the source flow controller 33. The air detector 70 can be used to detect air in the line 44 before it reaches the source flow controller 33. At that time, appropriate action can be taken by an operator to replace any empty reservoirs in the treatment solution source 60 or take any other suitable action needed to address the reason for air in the line 44.

If air is detected by the air detector 70, the control unit 41 (which is operably connected to the air detector 70 and the source flow controller 33) can, in some embodiments, be configured to operate the source flow controller 33 in reverse such that treatment solution in the line 44 can refill the fluid circuit back to the treatment solution source 60. In systems that are configured for such reverse operation, the intermediate containers downstream of the container selection controller 32 (e.g., first and second intermediate containers 11 and 12) should be filled from the bottom of the intermediate container such that treatment solution in the intermediate container can be withdrawn from the intermediate container through the same line used to fill the intermediate container during reverse operation of the source flow controller 33, with the withdrawn treatment solution being used in part to assist in the refilling of the fluid lines between the intermediate container (11 or 12) and the treatment solution source 60.

Still another optional feature found in the embodiments of the blood treatment apparatus 1 depicted in FIGS. 2, 5, and 8 is a sterilizing filter 80. The sterilizing filter 80 may be located in the fluid delivery path upstream of the container selection controller 32. In some embodiments, the sterilizing filter 80 may be located downstream from the source flow controller 33 (i.e., between the flow controller 33 and the container selection controller 32), although other locations are also possible (e.g., upstream of the flow controller 33). The sterilizing filter 80 is provided to reduce the likelihood of or delivering contaminated treatment solution to the container selection controller 32 for delivery to the intermediate containers used to supply the output controller 31.

The sterilizing filter 80 may, in some embodiments, include a vent (e.g., a passive vent in the form of a hydrophobic membrane) to assist with removal of air that may be entrained within the treatment solution.

The sterilizing filter 80 may, in some embodiments, be located downstream from the source flow controller 33. Placing the filter 80 downstream from the flow controller 33 may eliminate the development of a negative pressure within the line 44 feeding the flow controller 33 and any associated fluid degassing that could occur as a result.

In operation, the control units 41 in the illustrative embodiments of the blood treatment apparatus depicted in FIGS. 2, 5, and 8 may be capable of receiving weight information from the first gravimetric scale 21 and/or the second gravimetric scale 22, calculating the actual flow rate of the treatment solution delivered to the treatment solution port 10, comparing it with a selected constant flow rate or with a selected flow rate profile, and controlling the actual flow rate of the treatment solution using the fluid flow output controller 31, the source flow controller 33 and/or any other fluid flow control mechanisms (e.g., pumps, valves, clamps, etc.) that may be provided in the blood treatment apparatus described herein.

The control unit 41 may also be configured to receive weight information from the first gravimetric scale 21 and/or from the second gravimetric scale 22, determine the filling status of each intermediate container, and control, based on the filling status of each intermediate container, an alternating and successive intermediate container loading and unloading process during delivery of treatment solution to the treatment solution port 10. For example, the control unit 41 may be configured to receive weight information from the first gravimetric scale 21 and/or from the second gravimetric scale 22, detect the upper and lower threshold values for each of the intermediate containers (e.g., 11.2, 11.1, 12.2, 12.1), and control, based on the threshold values, an intermediate container loading and unloading procedure according to the following process: loading first intermediate container 11 to an upper limit threshold (e.g., 11.1) while unloading second intermediate container 12 until a lower limit threshold (e.g., 12.2) is detected for the second intermediate container 12, followed by unloading the first intermediate container 11 until its lower limit threshold (e.g., 11.2) is detected while loading the second intermediate container 12 to its upper limit threshold (e.g., 12.1).

For continuous delivery of treatment solution to the port 10, the rate of fluid flow from the source flow controller 33 should be greater than the rate at which the first intermediate container 11 and the second intermediate container 12 are unloaded (which corresponds to the flow rate of treatment solution being delivered through port 10 by the output controller 31). Maintaining that flow rate relationship should typically ensure that the intermediate container that is being loaded reaches its upper limit threshold before the intermediate container that is being unloaded reaches its lower limit threshold. If, in some embodiments, the flow rate of treatment solution delivered through the source flow controller 33 is less than the flow rate from the output controller 31 to the port 10, then flow through the port 10 will typically need to be halted occasionally to allow for refilling of the intermediate containers.

Referring to the illustrative embodiment of a blood treatment apparatus as depicted in FIGS. 2-4, the apparatus 1 includes the components related to the delivery of treatment solution in the blood treatment apparatus 1 that are common to the different embodiments described herein. Those common components include the first intermediate container 11, second intermediate container 12, first gravimetric scale 21, second gravimetric scale 22, output controller 31, container selection controller 32, source flow controller 33, control unit 41, treatment solution source 60, air detector 70, and sterilizing filter 80.

In this embodiment, the container selection controller 32 includes an outlet port 51 and an inlet port 52. Treatment solution flows into the container selection controller 32 from the treatment solution source 60 (through source flow controller 33) through the inlet port 52. Treatment solution flows out of the container selection controller 32 through the outlet port 51 where it flows into the output controller 31. The various components within the container selection controller 32 allow for the selective loading and unloading of the first intermediate container 11 and the second intermediate container 12 while also providing the ability to maintain a substantially continuous flow of treatment solution to the output controller 31 through the outlet port 51.

Within the container selection controller 32, first line 57 connects the outlet port 51 with each of the two output ports (53 and 55) of the first and second intermediate containers (11 and 12). Flow controllers (122 and 124) are provided to act on the first line 57 between the output ports (53 and 55)

and the outlet port 51 to either allow or prevent flow through the first line 57 to the outlet port 51. Although depicted schematically as clamps, the flow controllers (122 and 124) may be in the form of, e.g., valves, clamps, pumps, etc.

The container selection controller 32 depicted in FIG. 2 also includes a second line 58 that places the inlet port 52 into fluid communication with each of the two input ports (54 and 56) of the first and second intermediate containers (11 and 12). Flow controllers (121 and 123) are provided to act on the second line 58 between the inlet port 52 and the input ports (54 and 56) to either allow or prevent flow of treatment solution through the second line 58 to the input ports (54 and 56). Although depicted schematically as clamps, the flow controllers (121 and 123) may be in the form of, e.g., valves, clamps, pumps, etc.

In operation of the blood treatment apparatus 1, the first intermediate container 11 and the second intermediate container 12 are alternately loaded and unloaded by controlling the various flow controllers (121, 122, 13, 124) in the container selection controller 32 so that a substantially continuous flow of treatment solution can be provided to the outlet port 51 which feeds the output controller 31. FIGS. 3 and 4 depict operation of the blood treatment apparatus 1 such that the intermediate containers (11 and 12) can be alternately loaded and unloaded through the first and second lines (57 and 58).

In FIG. 3, the flow controller 121 is open and flow controller 123 is closed. As a result, treatment solution can flow into the first intermediate container 11 from the source flow controller 33 through second line 58, but is prevented from flowing into the second intermediate container 12 by the closed flow controller 123. Flow controller 122 on first line 57 is closed and flow controller 124 is open in the configuration depicted in FIG. 3. As a result, treatment solution can flow from the second intermediate container 12 to the output controller 31 through first line 57, but is prevented from flowing out of the first intermediate container 11 by the closed flow controller 122. The configuration depicted in FIG. 3 can, therefore, be described as a configuration in which the first intermediate container 11 is filled or loaded through second line 58 while the second intermediate container 12 is emptying or unloading through first line 57.

FIG. 4 depicts a different configuration for the blood treatment apparatus 1 of FIG. 2 in which the first intermediate container 11 is emptying or unloading while the second intermediate container 12 is filled or loaded. In particular, in the configuration of FIG. 4, the flow controller 123 is open and flow controller 121 is closed. As a result, treatment solution can flow into the second intermediate container 12 from the source flow controller 33 through second line 58, but is prevented from flowing into the first intermediate container 11 by the closed flow controller 121. Flow controller 124 is also closed and flow controller 122 is open in the configuration depicted in FIG. 4. As a result, treatment solution can flow from the first intermediate container 11 to the output controller 31 through first line 57, but is prevented from flowing out of the second intermediate container 12 by the closed flow controller 124.

In some embodiments, the control unit 41 may be configured to control the container selection controller 32 such that changeovers between the configurations depicted in FIGS. 3 and 4 be accomplished in a manner that provides for continuous flow of treatment solution to the output controller 31 and, thus, the port 10. For example, both flow controllers 122 and 124 on first line 57 be open at the same time before one of the flow controllers is closed when switching between the configurations depicted in FIGS. 3 and 4.

In some embodiments of the blood treatment apparatus described herein, a brief interruption (e.g., 60 seconds or less) in the flow of treatment solution to the output controller 31 may be tolerated and considered to fall within the definition of "substantially continuous" treatment solution delivery as described herein.

The control unit 41 may be configured to control the output controller 31 in different configurations. In one configuration, the control unit 41 controls the output controller 31, the container selection controller 32, and the source flow controller 33 to achieve a selected flow rate profile of treatment solution through the treatment solution port 10 based on weight information coming from either the first gravimetric scale 21 or the second gravimetric scale 22 when only one of the first intermediate container 11 or the second intermediate container 12 is being unloaded (while, e.g., the other intermediate container is being filled). In other words, the flow rate of treatment solution through the output controller 31 is a function of the rate of change in the amount of treatment solution in the first intermediate container 11 or the second intermediate container 12. Selection of the gravimetric scale (21 or 22) is based on which intermediate container (11 or 12) is being unloaded at that time.

In another configuration, the control unit 41 controls the output controller 31, the container selection controller 32, and the source flow controller 33 to achieve a selected flow rate profile of treatment solution through the treatment solution port 10 based on weight information coming from both the first and second gravimetric scales (21, 22). This configuration may be used when, e.g., the flow controllers 122 and 124 are both open such that treatment solution could be delivered to the first line 57 from both the first intermediate container 11 and the second intermediate container 12.

Referring to the illustrative embodiment of a blood treatment apparatus as depicted in FIGS. 5-7, the apparatus 1 includes the components related to the delivery of treatment solution in the blood treatment apparatus 1 that are common to the different illustrative embodiments described herein. Those common components include the first intermediate container 11, second intermediate container 12, first gravimetric scale 21, second gravimetric scale 22, output controller 31, container selection controller 32, source flow controller 33, control unit 41, treatment solution source 60, air detector 70, and sterilizing filter 80.

In this embodiment, the container selection controller 32 also includes an outlet port 51 and an inlet port 52. Treatment solution flows into the container selection controller 32 from the treatment solution source 60 (through source flow controller 33) through the inlet port 52. Treatment solution flows out of the container selection controller 32 through the outlet port 51 where it flows into the output controller 31. The various components within the container selection controller 32 allow for the selective loading and unloading of the first intermediate container 11 and the second intermediate container 12 while also providing the ability to maintain a substantially continuous flow of treatment solution to the output controller 31 through the outlet port 51.

Within the container selection controller 32, first line 57 connects the outlet port 51 with each of the two output ports (53 and 55) of the first and second intermediate containers (11 and 12). Flow controller 125 is provided to act on the first line 57 between the output ports (53 and 55) on the first and second intermediate containers (11 and 12) and the outlet port 51 to either allow or prevent flow through the first line 57 to the outlet port 51. The flow controller 125 may be in the form of, e.g., a multiport flow controller that is capable of being configured between at least two alternate configurations in which flow through first line 57 from one of the output ports (53 and 55) is allowed while flow through the first line 57 from the other output port is prevented. In some embodiments, the multiport flow controller 125 may have a third configuration in which flow through first line 57 from both of the output ports (53 and 55) is allowed. The multiport flow controller 125 may be provided in the form of a multiport valve, a clamp assembly, etc. In some embodiments, the multiport flow controller 125 may be operably linked to the control unit 41 as depicted in FIG. 5 such that the control unit 41 can be used to switch the multiport flow controller 125 between its various configurations.

The container selection controller 32 depicted in FIG. 5 also includes a second line 58 that places the inlet port 52 into fluid communication with each of the two input ports (54 and 56) of the first and second intermediate containers (11 and 12). A flow controller 126 is provided to either allow or prevent flow of treatment solution through the second line 58. The flow controller 126 may be in the form of, e.g., a multiport flow controller that is capable of being configured between at least two alternate configurations in which flow through second line 58 to one of the input ports (54 and 56) is allowed while flow through the second line 58 to the other input port is prevented. In some embodiments, the multiport flow controller 126 may have a third configuration in which flow through second line 58 to both of the input ports (54 and 56) is allowed. The multiport flow controller 126 may be provided in the form of a multiport valve, a clamp assembly, etc. In some embodiments, the multiport flow controller 126 may be operably linked to the control unit 41 as depicted in FIG. 5 such that the control unit 41 can be used to switch the multiport flow controller 126 between its various configurations.

In operation of the blood treatment apparatus 1, the first intermediate container 11 and the second intermediate container 12 are alternately loaded and unloaded by controlling the flow controllers (125 and 126) in the container selection controller 32 so that a substantially continuous flow of treatment solution can be provided to the outlet port 51 which feeds the output controller 31. FIGS. 6 and 7 depict operation of the blood treatment apparatus 1 such that the intermediate containers (11 and 12) can be alternately loaded and unloaded through the first and second lines (57 and 58).

In FIG. 6, the flow controller 126 is configured to allow treatment solution to flow into the first intermediate container 11 from the source flow controller 33 through second line 58, while preventing treatment solution from flowing into the second intermediate container 12. Flow controller 125 is, in the embodiment depicted in FIG. 6, configured to allow treatment solution to flow from the second intermediate container 12 to the output controller 31 through first line 57, while preventing treatment solution from flowing out of the first intermediate container 11. The configuration depicted in FIG. 6 can, therefore, be described as a configuration in which the first intermediate container 11 is filled or loaded through second line 58 while the second intermediate container 12 is emptying or unloading through first line 57.

FIG. 7 depicts a different configuration for the blood treatment apparatus 1 of FIG. 5 in which the first intermediate container 11 is emptying or unloading while the second intermediate container 12 is filled or loaded. In particular, in the configuration of FIG. 7, the flow controller 126 is configured such that treatment solution can flow into the second intermediate container 12 from the source flow controller 33 through second line 58, while treatment solution is prevented from flowing into the first intermediate container 11. Flow controller 125 is, in the embodiment depicted in FIG. 7, configured to allow treatment solution to flow from the first intermediate container 11 to the output controller 31 through first line 57, while treatment solution is prevented from flowing out of the second intermediate container 12 through first line 57. The configuration depicted in FIG. 7 can, therefore, be described as a configuration in which the first intermediate container 11 is emptying or unloading through first line 57 while the second intermediate container 12 is loading or filling through second line 58.

In some embodiments, the control unit 41 may be configured to control the container selection controller 32 such that changeovers between the configurations depicted in FIGS. 6 and 7 be accomplished in a manner that does not interrupt the flow of treatment solution to the output controller 31. For example, in some embodiments the flow controller 125 may allow treatment solution from both the first intermediate container 11 and the second intermediate container 12 to flow through first line 57 to the treatment solution output flow controller 31 when switching between the configurations depicted in FIGS. 6 and 7.

The control unit 41 may be configured to control the output controller 31 in different configurations. In one configuration, the control unit 41 controls the output controller 31, the container selection controller 32, and the source flow controller 33 to achieve a selected flow rate profile of treatment solution through the treatment solution port 10 based on weight information coming from either the first gravimetric scale 21 or the second gravimetric scale 22 when only one of the first intermediate container 11 or the second intermediate container 12 is being unloaded (while, e.g., the other intermediate container is being filled). In other words, the flow rate of treatment solution through the output controller 31 is a function of the rate of change in the amount of treatment solution in the first intermediate container 11 or the second intermediate container 12. Selection of the gravimetric scale (21 or 22) is based on which intermediate container (11 or 12) is being unloaded at that time.

In another configuration, the control unit 41 controls the output controller 31, the container selection controller 32, and the source flow controller 33 to achieve a selected flow rate profile of treatment solution through the treatment solution port 10 based on weight information coming from both the first and second gravimetric scales (21, 22). This configuration may be used if, e.g., the flow controller 125 allows treatment solution to flow through the first line 57 from both the first intermediate container 11 and the second intermediate container 12.

In general terms the output controller 31 is configured to deliver the treatment solution through the treatment solution port at a dialysis fluid flow rate; to achieve this goal the control unit 41 is configured to receive a set value for the dialysis fluid flow rate (for example from a user interface provided to receive the set value for the dialysis fluid flow rate from an operator) and thereafter to control the output controller 31 to cause the treatment solution to flow at the dialysis fluid flow rate in correspondence of the treatment solution port 10.

In other terms, the dialysis fluid flow rate is set by the physician at the beginning of the treatment and the machine is controlled so that the output controller (i.e. the pump) is driven to tend to deliver the flow which was set.

In more detail, the control unit 41 is configured to control the output controller 31 to cause the treatment solution to flow at the dialysis fluid flow rate based on the weight signals from the first and second gravimetric scales 21, 22.

In the first mode in which the first intermediate container 11 is providing fluid to the filter and/or to the blood directly the control unit 41 is configured to control the output controller 31 to cause the treatment solution to flow at the dialysis fluid flow rate based on the weight signal from the first gravimetric scale 21. In the first mode the weight signal from the other scale 22 is used to monitor replenishment with fresh treatment fluid through the source flow controller; therefore in the first mode the control unit 41 is configured to control the output controller 31 without using the weight signal from the second gravimetric scale 22.

In the second mode in which the second intermediate container 12 is providing fluid to the filter and/or to the blood directly, the control unit 41 is configured to control the output controller 31 to cause the treatment solution to flow at the dialysis fluid flow rate based on the weight signal from the second gravimetric scale 22.

In the second mode the weight signal from the other scale 21 is used to monitor replenishment with fresh treatment fluid through the source flow controller 33; therefore in the second mode the control unit 41 is configured to control the output controller 31 without using the weight signal from the first gravimetric scale 21.

To achieve the treatment prescription the control unit 41 is configured to alternatively switch a plurality of times between the first and the second mode during a treatment session.

Moreover, in general the control unit 41 is configured during treatment to control the source flow controller 33 to provide a fluid flow rate higher (or at most equal) to a dialysis fluid flow rate provided by the output controller 31.

Another feature depicted in connection with the embodiment of the blood treatment apparatus 1 of FIG. 5 is the treatment solution source 60 which, rather than including a plurality of reservoirs of treatment solution as described in connection with the embodiment depicted in FIG. 2, includes a liquid source 67, treatment solution precursor 68, and mixing apparatus 69 configured to combine liquid from the liquid source 67 (e.g., water, a suitable aqueous solution, etc.) and the treatment solution precursor 68 (e.g., a concentrated solution of dialysate, etc.) to form the treatment solution. Unlike the treatment solution source 60 of FIG. 2, the treatment solution delivered using the treatment solution source 60 of FIG. 5 is not provided in reservoirs, but is, instead, constituted within the treatment solution source 60.

Referring to the illustrative embodiment of a blood treatment apparatus as depicted in FIGS. 8-10, the apparatus 1 includes the components related to the delivery of treatment solution in the blood treatment apparatus 1 that are common to the different illustrative embodiments described herein. Those common components include the first intermediate container 11, second intermediate container 12, first gravimetric scale 21, second gravimetric scale 22, output controller 31, container selection controller 32, source flow controller 33, control unit 41, treatment solution source 60, air detector 70, and sterilizing filter 80.

In the embodiment depicted in FIGS. 8-10, gravity is used to, in part, control the loading and unloading of the first intermediate container 11 and the second intermediate container 12. In particular, the vertical position of the first intermediate container 11 relative to the second intermediate container 12 is used in combination with the container selection controller 32, the output controller 31 and the source flow controller 33 by the control unit to selectively load and unload the first and second intermediate containers 11 and 12.

The source flow controller 33 is connected to the output controller 31 through a fluid line 157. The first intermediate container 11 is in fluid communication with the fluid line 157 through fluid line 152 which connects to fluid line 157 at junction 153. The second intermediate container 12 is in fluid communication with fluid line 157 through fluid line 154 which connects with fluid line 157 at junction 155. The container selection controller 32 is, in the depicted embodiment, positioned along fluid line 157 between junctions 153 and 155.

Gravity is used in the blood treatment apparatus one depicted in FIG. 8 by positioning the first intermediate container 11 at a higher vertical location than the second intermediate container 12. In some embodiments, the upper limit (e.g., 12.1) of the second intermediate container 12 is located lower or at the same level as the lower limit (e.g., 11.2) of the first intermediate container 11. In operation of the blood treatment apparatus 1, the first intermediate container 11 and the second intermediate container 12 are alternately loaded and unloaded by controlling the container selection controller 32 along with the source flow controller 33 so that a substantially continuous flow of treatment solution can be provided to the output controller 31.

FIGS. 9 and 10 depict operation of the blood treatment apparatus 1 depicted in FIG. 8 such that the intermediate containers (11 and 12) can be alternately loaded and unloaded through fluid lines 152, 154 and 157. In FIG. 9, the container selection controller 32 is closed. As a result, treatment solution flows into the first intermediate container 11 from the source flow controller 33 through fluid lines 152 and 157, while treatment solution is prevented from flowing past the container selection controller 32 to either second intermediate container 12 or the output controller 31. As a result, treatment solution from the source flow controller 33 fills or loads the first intermediate container 11 in the configuration depicted in FIG. 9. With container selection controller 32 closed in FIG. 9, the treatment solution in the second intermediate container 12 flows out of the second intermediate container 12 to the output controller 31. The configuration depicted in FIG. 9 can, therefore, be described as a configuration in which the first intermediate container 11 is filled or loaded while the second intermediate container 12 is emptying or unloading.

FIG. 10 depicts a different configuration for the blood treatment apparatus 1 of FIG. 8 in which the first intermediate container 11 is emptying or unloading while the second intermediate container 12 is filled or loaded with treatment solution. In particular, in the configuration of FIG. 10, the source flow controller 33 is stopped or closed so that no treatment solution is being delivered into the fluid line 157 through the flow controller 33 and the container selection controller 32 is open. Because the first intermediate container 11 is higher than the second intermediate container 12, treatment solution will flow into the fluid line 157 from the first intermediate container 11 to deliver treatment solution to both the output controller 31 and the second intermediate container 12. The treatment solution introduced into fluid line 157 from the first intermediate container 11 in excess of that removed from fluid line 157 by the output controller 31 will flow into the second intermediate container 12. The configuration depicted in FIG. 10 can, therefore, be described as a configuration in which the first intermediate container 11 is emptying or unloading through fluid line 157 while the second intermediate container 12 is loading or filling.

To ensure continuous flow of treatment solution through the output controller 31, some flow rate conditions must be met for the three following flow rates: the flow rate from the source flow controller 33 ($Q33$), the flow rate through the output controller 31 ($Q31$), and the mean of the gravity-driven flow rate of treatment solution from the first intermediate container 11 to the second intermediate container 12 over the refill cycle time ($Q2g$) (this flow through line 154 into the second intermediate container 12 is present only in the operating configuration depicted in FIG. 10).

Two conditions that should be met for continuous flow through the output controller 31 are: 1) the source flow should be greater than the output flow, i.e., $Q33>Q31$; and 2) the gravity-driven flow rate $Q2g$ is large enough to fill the second intermediate container 12 in a timely manner while still feeding the output controller 31, i.e., $Q2g>(Q31/(Q33/Q32-1)$.

If the flow from the source flow controller 33 is above three times the flow rate through the output controller 31 (i.e., $Q33>(3\times Q31)$), then the gravity-driven flow rate of treatment solution from the first intermediate container 11 to the second intermediate container 12 ($Q2g$) should be at least half of the desired flow rate through the output controller 31 (i.e., $Q2g\geq(Q31/2)$.

If the flow from the source flow controller 33 is above 1.5 times the flow rate through the output controller 31 (i.e., $Q33>(1.5\times Q31)$), then the gravity-driven flow rate of treatment solution from the first intermediate container 11 to the second intermediate container 12 ($Q2g$) should be at least twice the desired flow rate through the output controller 31 (i.e., $Q2g\geq(2\times Q31)$).

Figure 11:
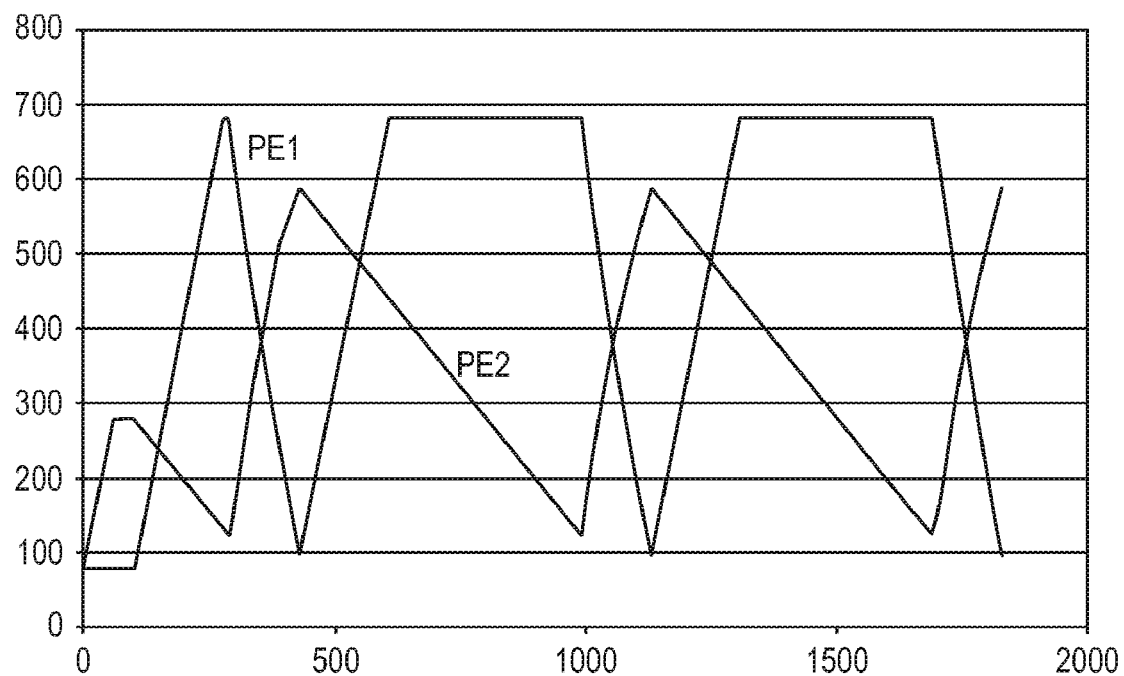
FIG. 11 depicts the weight changes of the intermediate containers in the embodiment of FIG. 8 during operation of the blood treatment apparatus.

FIG. 11 represents, for the embodiment of the blood treatment apparatus depicted in FIGS. 8-10, the weight changes of the first and second intermediate containers according to the treatment time, where time (in seconds) is represented along the X or horizontal axis and weight (in grams) is represented along the Y or vertical axis.

The succession of the two phases or steps during the draining cycle, preceded by a system-priming phase will now be explained, starting from the particular example of FIG. 11. At the start of the session, the two intermediate containers are almost empty (e.g., a weight of approximately 80 grams (g)) is recorded and a priming phase is implemented.

The control unit primes the source flow controller 33, opens the container selection controller 32, and does not operate the output controller 31 such that no treatment solution is removed from fluid line 157 by the fluid output controller 31.

The source flow controller 33 controls the flow of treatment solution into the fluid line 157 from the treatment solution source 60.

The second intermediate container 12 is downstream from the source flow controller 33 in relation to the first intermediate container 11, but is located at a position that is lower than the first intermediate container 11. Because it is lower than the first intermediate container 11, the second intermediate container 12 is loaded with treatment solution before the first intermediate container 11. Thus, it may be seen that the weight of the second intermediate container 12 (PE2 on FIG. 11) increases regularly in priority relative to the weight of the first intermediate container 11 (PE1 on FIG. 11), which remains unchanged.

As the second intermediate container 12 reaches a selected weight (e.g., approximately 280 g in the depicted embodiment), the blood treatment apparatus 1 will operate according to a first phase as depicted in FIG. 9: The source flow controller 33 continues to deliver treatment solution, the container selection controller 32 is closed, and the output controller 31 can be operated to deliver treatment solution to the port 10.

As seen in FIG. 9, the second intermediate container 12 will unload into the fluid line 157 where the treatment solution will be delivered to the output controller 31 for, e.g., the start of a therapy session. It may be seen that the weight of the second intermediate container 12 regularly decreases (e.g., from approximately 280 g to approximately 120 g).

As also seen in FIG. 9, the first intermediate container 11 is loaded with the treatment solution coming from the source flow controller 33. A weight increase of the first intermediate container 11, e.g., from 80 g to approximately 680 g, can be seen.

This first phase is performed until a minimum weight threshold of the second intermediate container 12 (e.g., approx. 120 g in the depicted embodiment) is reached, or a maximum weight threshold of the first intermediate container (e.g., 680 g in the depicted embodiment) is reached, or the first of the two above-mentioned thresholds is reached.

When such a threshold is detected, the control unit controls the entry into the second phase, which is depicted in FIG. 10.

In the second phase, treatment solution flows out of the first intermediate container 11 (as indicated by the decline in weight of the first intermediate container 11) while treatment solution flows into the second intermediate container 12 (as indicated by the increase in weight of the second intermediate container 12). In this phase, the control unit 41 opens the container selection controller 32 and stops the flow of treatment solution from the source flow controller 33 (in some embodiments, the source flow controller 33 is stopped before the container selection controller 32 is opened). As a result, treatment solution from the first intermediate container 11 flows into the second intermediate container 12 and to the output controller 31.

This second phase continues until the first intermediate container 11 reaches a selected minimum weight (e.g., approx. 100 g in the depicted embodiment) or the second intermediate container 12 reaches a selected maximum weight (e.g., approx. 590 g in the depicted embodiment).

At the end of the second phase, the system switches back to the first phase in which the source flow controller 33 delivers treatment solution and the container selection controller 32 is closed while the output controller 31 delivers treatment solution to the port 10.

With the container selection controller 32 closed, the second intermediate container 12 unloads treatment solution that is delivered to the output controller 31 to continue the therapy session. It may be seen that the weight of the second intermediate container 12 regularly decreases (e.g., from approximately 590 g to approximately 120 g).

On the other hand, the first intermediate container 11 is loaded with the treatment solution coming from the source flow controller 33. A weight increase of the first intermediate container 11, e.g., from 80 g to approximately 680 g, can be seen.

It should be noted that the first intermediate container 11 reaches its selected maximum threshold (e.g., approx. 680 g) before the second container 12 reaches its selected minimum threshold. As a result, delivery of treatment solution into the first intermediate container 11 is halted as indicated by the steady-state (constant) weight of the first intermediate container in FIG. 11. Alternatively, the switch back to second phase operation could be triggered at any time after the first intermediate container 11 reaches its selected maximum threshold (which would occur before the second intermediate container reaches its selected minimum threshold, e.g., at about 400 g or less in the embodiment depicted in FIG. 11).

When the minimum weight threshold of the second container is reached, the system can then enter the second phase operation as described herein, with switches between the first and second phases being based on the minimum and maximum thresholds for the first and second intermediate containers 11 and 12 until the end of a therapy session is reached.

Illustrative embodiments of the blood treatment apparatus and methods of using the same are discussed and reference has been made to possible variations. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A method of controlling treatment solution flow in a blood treatment apparatus, wherein the blood treatment apparatus comprises:
   a blood circuit that includes an arterial line intended to draw blood from a patient and a venous line intended to return blood to the patient;
   a filter, having a primary chamber and a secondary chamber separated by a semi- permeable membrane; and
   a drain line exiting the secondary chamber to remove spent dialysate from the secondary chamber;
   the method comprising:
   filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level;
   delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level;
   driving the output controller to deliver treatment solution to at least one of the secondary chamber and the blood circuit through a treatment solution port; and
   passing treatment solution delivered to the treatment solution port from the treatment solution source through a sterilizing filter.

2. A method according to claim 1, the method further comprising:
   controlling a source flow controller to deliver treatment solution from the treatment solution source to at least one of the first intermediate container and the second intermediate container;
   controlling the source flow controller and the output controller in a first mode in which treatment solution is delivered to the output controller while treatment solution leaves the first intermediate container and the second intermediate container fills with treatment solution, wherein treatment solution flows into the second intermediate container from the source flow controller while treatment solution is prevented from flowing into the first intermediate container and treatment solution flows from the first intermediate container to the output controller while treatment solution is prevented from flowing out of the second intermediate container to the output controller;
   controlling the source flow controller and the output controller in a second mode in which the second intermediate container delivers treatment solution to the output controller while the first intermediate container fills with treatment solution from the treatment solution source, wherein treatment solution flows into the first intermediate container from the source flow controller while treatment solution is prevented from flowing into the second intermediate container and treatment solution can flow from the second intermediate container to the output controller while treatment solution is prevented from flowing out of the first intermediate container to the output controller.

3. A method according to claim 2, wherein, in the first mode, the method comprises driving the output controller to cause the treatment solution to flow at a selected dialysis fluid flow rate based on the weight of the first intermediate container.

4. A method according to claim 2, wherein, in the second mode, the method comprises driving the output controller to cause the treatment solution to flow at a selected dialysis fluid flow rate based on the weight of the second intermediate container.

5. A method according to claim 2, wherein the method further comprises switching a plurality of times between the first mode and the second mode during a treatment session.

6. A method according to claim 2, wherein the method comprises providing a continuous flow of treatment solution to the treatment solution port when switching between the first mode and the second mode.

7. A method according to claim 2, wherein the method further comprises, in the first mode, controlling the source flow controller to cause filling of the second intermediate container with the treatment solution based on the weight of the second intermediate container and without regard to the weight of the first intermediate container.

8. A method according to claim 2, wherein the method further comprises, in the second mode, controlling the source flow controller to cause filling of the first intermediate container with the treatment solution based on the weight of the first intermediate container and without regard to the weight of the second intermediate container.

9. A method according to claim 1, the method further comprising:
   filling the second intermediate container with treatment solution by delivering treatment solution from the treatment solution source to the second intermediate container, weighing the second intermediate container to determine when the amount of treatment solution in the second intermediate container has risen to a selected fill level, and halting the delivery of treatment solution to the second intermediate container when the amount of treatment solution in the second intermediate container has risen to the selected fill level; and delivering treatment solution from the first intermediate container to the output controller while filling the second intermediate container from the treatment solution source, weighing the first intermediate container to determine when the amount of treatment solution in the first intermediate container has fallen to a selected refill level, and halting the delivery of treatment solution to the output controller when the amount of treatment solution in the first intermediate container has fallen to the selected refill level.

10. A method according to claim 1, wherein the treatment solution source comprises a plurality of supply reservoirs containing treatment solution, and wherein the method further comprises replacing one or more supply reservoirs of the plurality of supply reservoirs while filling the first intermediate container.

11. A method according to claim 1, wherein filling the first intermediate container comprises pumping treatment solution from the treatment solution source through a source flow controller to the first intermediate container.

12. A method according to claim 1, wherein a volume of treatment solution delivered to the output controller from the second intermediate container is calculated based on weight of the second intermediate container.

13. A method according to claim 1, wherein the method further comprises driving the output controller to cause the treatment solution to flow through the treatment solution port at a selected dialysis fluid flow rate.

14. A method according to claim 13, wherein the method further comprises driving the output controller to cause the treatment solution to flow at the dialysis fluid flow rate based on the weight of the second intermediate container.

15. A method according to claim 1, wherein the method further comprises driving the output controller without regard to the weight of the second intermediate container.

16. A method according to claim 1, wherein the method further comprises driving the output controller without regard to the weight of the first intermediate container.

17. A method according to claim 1, wherein the method further comprises treatment solution from the treatment solution source to the first intermediate container at a fluid flow rate equal to or greater than a dialysis fluid flow rate at which the output controller delivers treatment solution to the treatment solution port.

18. A method according to claim 1, wherein treatment solution delivered to the first intermediate container from the treatment solution source passes through a source flow controller.

19. A method according to claim 1, wherein the method further comprises removing air entrained within the treatment solution with a vent comprising a hydrophobic membrane.

20. A method according to claim 1, wherein the method further comprises calculating, from the weights of the first intermediate container and the second intermediate container, a volume of treatment solution delivered to the output controller from both the first intermediate container and the second intermediate container.

21. A method according to claim 1, wherein the method further comprises passing treatment solution through an air detector located between the treatment solution source and the treatment solution port.

22. A method of controlling treatment solution flow in a blood treatment apparatus, wherein the blood treatment apparatus comprises:
a blood circuit that includes an arterial line intended to draw blood from a patient and a venous line intended to return blood to the patient;
a filter, having a primary chamber and a secondary chamber separated by a semi- permeable membrane; and
a drain line exiting the secondary chamber to remove spent dialysate from the secondary chamber;
the method comprising:
filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level, wherein the treatment solution source comprises a plurality of supply reservoirs containing treatment solution;
delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level;
replacing one or more supply reservoirs of the plurality of supply reservoirs while filling the first intermediate container; and
driving the output controller to deliver treatment solution to at least one of the secondary chamber and the blood circuit through a treatment solution port.

23. A method of controlling treatment solution flow in a blood treatment apparatus, wherein the blood treatment apparatus comprises:
a blood circuit that includes an arterial line intended to draw blood from a patient and a venous line intended to return blood to the patient;
a filter, having a primary chamber and a secondary chamber separated by a semi- permeable membrane; and
a drain line exiting the secondary chamber to remove spent dialysate from the secondary chamber;
the method comprising:
filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level;
delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level;

removing air entrained within the treatment solution with a vent comprising a hydrophobic membrane; and driving the output controller to deliver treatment solution to at least one of the secondary chamber and the blood circuit through a treatment solution port.

24. A method of controlling treatment solution flow in a blood treatment apparatus, wherein the blood treatment apparatus comprises:

a blood circuit that includes an arterial line intended to draw blood from a patient and a venous line intended to return blood to the patient;

a filter, having a primary chamber and a secondary chamber separated by a semi- permeable membrane; and a drain line exiting the secondary chamber to remove spent dialysate from the secondary chamber;

the method comprising:

filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level;

delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level;

passing treatment solution through an air detector located between the treatment solution source and the treatment solution port; and driving the output controller to deliver treatment solution to at least one of the secondary chamber and the blood circuit through a treatment solution port.

25. A method of controlling treatment solution flow in a blood treatment apparatus, wherein the blood treatment apparatus comprises:

a blood circuit that includes an arterial line intended to draw blood from a patient and a venous line intended to return blood to the patient;

a filter, having a primary chamber and a secondary chamber separated by a semi-permeable membrane; and a drain line exiting the secondary chamber to remove spent dialysate from the secondary chamber;

the method comprising:

filling a first intermediate container with treatment solution by delivering treatment solution from a treatment solution source to the first intermediate container, weighing the first intermediate container to determine when the amount of treatment solution in the first intermediate container has risen to a selected fill level, and halting the delivery of treatment solution to the first intermediate container when the amount of treatment solution in the first intermediate container has risen to the selected fill level;

delivering treatment solution from a second intermediate container to an output controller while filling the first intermediate container from the treatment solution source, weighing the second intermediate container to determine when the amount of treatment solution in the second intermediate container has fallen to a selected refill level, and halting the delivery of treatment solution to the output controller when the amount of treatment solution in the second intermediate container has fallen to the selected refill level;

controlling a source flow controller to deliver treatment solution from the treatment solution source to at least one of the first intermediate container and the second intermediate container;

controlling the source flow controller and the output controller in a first mode in which treatment solution is delivered to the output controller while treatment solution leaves the first intermediate container and the second intermediate container fills with treatment solution, wherein treatment solution flows into the second intermediate container from the source flow controller while treatment solution is prevented from flowing into the first intermediate container and treatment solution flows from the first intermediate container to the output controller while treatment solution is prevented from flowing out of the second intermediate container to the output controller;

controlling the source flow controller and the output controller in a second mode in which the second intermediate container delivers treatment solution to the output controller while the first intermediate container fills with treatment solution from the treatment solution source, wherein treatment solution flows into the first intermediate container from the source flow controller while treatment solution is prevented from flowing into the second intermediate container and treatment solution can flow from the second intermediate container to the output controller while treatment solution is prevented from flowing out of the first intermediate container to the output controller; and driving the output controller to deliver a continuous flow of treatment solution to at least one of the secondary chamber and the blood circuit through a treatment solution port.

26. A method according to claim 25, wherein the treatment solution source comprises a plurality of supply reservoirs containing treatment solution, and wherein the method further comprises replacing one or more supply reservoirs of the plurality of supply reservoirs while filling the first intermediate container.

* * * * *